United States Patent
Ueno et al.

(10) Patent No.: US 9,869,615 B2
(45) Date of Patent: Jan. 16, 2018

(54) SAMPLE DISPERSION DEVICE AND SAMPLE DISPERSION METHOD

(71) Applicant: HORIBA, Ltd., Kyoto-shi, Kyoto (JP)

(72) Inventors: Kusuo Ueno, Kyoto (JP); Tomoya Shimizu, Kyoto (JP)

(73) Assignee: HORIBA, LTD., Kyoto (JP)

( * ) Notice: Subject to any disclaimer, the term of this patent is extended or adjusted under 35 U.S.C. 154(b) by 0 days.

(21) Appl. No.: 15/304,245

(22) PCT Filed: Apr. 14, 2015

(86) PCT No.: PCT/JP2015/061408
§ 371 (c)(1),
(2) Date: Oct. 14, 2016

(87) PCT Pub. No.: WO2015/159870
PCT Pub. Date: Oct. 22, 2015

(65) Prior Publication Data
US 2017/0045426 A1    Feb. 16, 2017

(30) Foreign Application Priority Data
Apr. 18, 2014 (JP) ................. 2014-086110

(51) Int. Cl.
*G01N 1/28* (2006.01)
(52) U.S. Cl.
CPC .................... *G01N 1/286* (2013.01)
(58) Field of Classification Search
CPC .................... G01N 1/20; G01N 1/00
USPC ........................ 73/863.81, 864.81
See application file for complete search history.

(56) References Cited

U.S. PATENT DOCUMENTS

| | | | |
|---|---|---|---|
| 4,868,128 A | 9/1989 | Sommer et al. | |
| 5,286,451 A * | 2/1994 | De Silva | G01N 1/14 356/36 |
| 5,770,152 A * | 6/1998 | Schuster | G01N 7/10 422/421 |
| 6,739,207 B2 * | 5/2004 | Sjoquist | G01N 1/286 73/864.81 |
| 6,918,310 B2 * | 7/2005 | Bjork | G01N 1/20 73/863.81 |

FOREIGN PATENT DOCUMENTS

| | | | |
|---|---|---|---|
| JP | 62-210073 A | 9/1987 | |
| JP | 63-502213 A | 8/1988 | |

(Continued)

OTHER PUBLICATIONS

International Search Report dated Jun. 16, 2015 for PCT/JP2015/061408 and English translation.

*Primary Examiner* — Jewel V Thompson
(74) *Attorney, Agent, or Firm* — Lucas & Mercanti, LLP (57) ABSTRACT

A sample dispersion device capable of preparing a measurement sample in the most suitable dispersion state without repreparing the measurement sample many times, is one that by introducing sample particles into a container and injecting the sample particles in the container using a pressure difference, disperses sample particles onto a holding member provided in a container to make the holding member hold the sample particles. The holding member has a holding surface made to hold the sample particles; and the holding surface has multiple portions having mutually different tilt angles.

8 Claims, 6 Drawing Sheets

(56) References Cited

FOREIGN PATENT DOCUMENTS

| | | |
|---|---|---|
| JP | 05-060666 A | 3/1993 |
| JP | 09-133613 A | 5/1997 |
| JP | 2001325911 A | 11/2001 |
| JP | 3530453 B2 | 5/2004 |
| JP | 2008292292 A | 12/2008 |
| JP | 2010527455 A | 8/2010 |
| WO | 2008142387 A1 | 11/2008 |

* cited by examiner

SAMPLE DISPERSION DEVICE AND SAMPLE DISPERSION METHOD

CROSS REFERENCE TO RELATED APPLICATION

This Application is a 371 of PCT/JP2015/061408 filed on Apr. 14, 2015, which, in turn, claimed the priority of Japanese Patent Application No. JP 2014-086110 filed on Apr. 18, 2014, both applications are incorporated herein by reference.

CROSS-REFERENCE TO RELATED APPLICATIONS

The present invention claims priority to JP 2014-086110, filed Apr. 18, 2014.

BACKGROUND OF THE INVENTION

The present invention relates to a sample dispersion device and sample dispersion method adapted to prepare a measurement sample that is to be observed with an electron microscope such as an SEM or a device such as an optical microscope.

In the past, in order to observe sample particles with an electron microscope, a measurement sample in which the sample particles are uniformly dispersed on a sample plate has been prepared. As a device adapted to uniformly disperse the sample particles on the sample plate, there is one described in, for example, Patent Literature 1.

The device described in Patent Literature 1 includes: a container; a sample introduction pipe penetrating through the container; and a valve adapted to open/close the inside of the sample introduction pipe. In addition, by closing the valve to depressurize the inside of the container and opening the valve after bringing the inside of the container into a vacuum state, sample particles under atmospheric pressure are vigorously and uniformly dispersed into the vacuum container through the sample introduction pipe.

CITATION LIST

Patent Literature

Patent Literature 1: Japanese Patent No. 3530453

Meanwhile, depending on the size and/or shape of sample particles dispersed in a measurement sample, the dispersion state of the sample particles becomes sparse or dense. For this reason, in order to prepare a measurement sample suitable for observation, it is necessary to change the dispersion state in accordance with the particle size and/or shape of sample particles.

However, the sample dispersion device described in Patent Literature 1 has a problem that a measurement sample has to be reprepared many times until a measurement sample suitable for observation can be prepared.

Also, whether or not the most suitable dispersion state is achieved cannot be visually confirmed but can be confirmed only by observation using an electron microscope, thus also causing the problem that an operator moves back and forth between the sample dispersion device and the electron microscope only for preparing the measurement sample, and as a result, an excessive burden is placed on the operator.

BRIEF SUMMARY OF THE INVENTION

The present invention is made in consideration of the above-described problems, and mainly intends to provide a sample dispersion device capable of preparing a measurement sample in the most suitable dispersion state without repreparing the measurement sample many times.

Solution to Problem

The sample dispersion device of the present invention is a sample dispersion device that by introducing sample particles into a container and injecting the sample particles in the container using a pressure difference, disperses sample particles onto a holding member provided in the container to make the holding member hold the sample particles, in which the holding member has a holding surface made to hold the sample particles and the holding surface has multiple portions having mutually different tilt angles.

In the above-described configuration, in order to provide a density gradient to the dispersion state of the sample particles, the sample particles are injected and introduced into the container, and the multiple portions having mutually different tilt angles are provided on the holding surface of the holding member. This configuration makes it possible to provide a density gradient to the dispersion state of the sample particles because when the sample particles uniformly diffused by the injection are held by the holding member, the amount of sample particles to be held changes depending on a tilt angle of the holding surface. For this reason, by changing an observation area of the holding member in an electron microscope, a dispersion state most suitable for observation can be obtained, and therefore a measurement sample can be prepared by dispersing once without repreparing the measurement sample many times. Also, since the sample particles are injected, the sample particles can be dispersed onto the holding member faster than spontaneous precipitation, and also the sample particles can be prevented from being classified.

In addition, as one specific embodiment of the sample dispersion device according to the present invention, one in which the multiple portions formed on the holding surface are mutually adjacently arranged, and have a predetermined length in a direction perpendicular to a direction of the mutually adjacent arrangement can be cited. More specifically, one in which the holding member forms a partially cylindrical shape can be cited.

By configuring as described above, since the holding surface of the holding member holds the sample particles in continuously different dispersion states, an operator can observe the dispersion states stepwise, and easily make the observation with an electron microscope. Also, since the multiple portions have the predetermined length in the direction perpendicular to the direction of the mutually adjacent arrangement, an observation area of sample particles dispersed in the same dispersion state can be expanded. In addition, as long as the holding member is one forming the partially cylindrical shape, the density of sample particles can be continuously changed and also the dispersion state can be more finely changed, and therefore a measurement sample in a dispersion state more suitable for the observation can be prepared by dispersing once.

Further, the sample dispersion device of the present invention can change the density gradient of sample particles only by changing the shape of the holding member, and therefore without changing the device configuration of a conventional sample dispersion device described in, for example, Patent Literature 1, measurement samples having different sample particle dispersion states can be prepared using the conventional device. For this reason, a measurement sample suitable for observation can be easily prepared without placing an excessive burden on an operator.

A sample dispersion method of the present invention is a sample dispersion method that introduces sample particles into a container, and disperses sample particles onto a holding member provided in the container to make the holding member hold the sample particles, and the sample dispersion method includes: an injection step of injecting the sample particles into the container using a pressure difference; and a holding step of making the holding member hold the injected sample particles, in which in the holding step, the holding member provided with a holding surface having multiple portions having mutually different tilt angles is made to hold the sample particles.

Meanwhile, as the sample dispersion device of the present invention, a sample dispersion device that introduces sample particles into a container, and disperses sample particles onto a holding member provided in the container to make the holding member hold the sample particles, in which the holding member has a holding surface made to hold the sample particles, and that includes a density change mechanism adapted to make an electric field act on the sample particles introduced into the container, and thereby on the holding surface, form multiple holding areas where the densities of sample particles to be held are different is also possible.

The above-described configuration includes the density change mechanism in order to provide a density gradient to the dispersion state of the sample particles, and therefore also makes it possible to prepare a measurement sample in the most suitable dispersion state by dispersing once without repreparing the measurement sample many times because the density change mechanism changes the dispersion state of the sample particles.

As one specific embodiment of the above-described sample dispersion device, one further including a sample introduction part for introducing the sample particles into the container, in which the density change mechanism is arranged between the sample introduction part and the holding member and applied with voltage at a potential opposite to that of the sample particles can be cited.

By configuring as described above, the density change mechanism arranged between the sample introduction part and the holding member can collect sample particles and change the amount of the collected sample particles by changing the voltage, and therefore the density of sample particles to be held on the holding member can be changed to change the dispersion state.

In this case, multiple holding members may be prepared to form multiple measurement samples having mutually different sample particle dispersion states, or one measurement sample in which multiple portions having different dispersion states is provided on one holding member may be formed.

As another specific embodiment of the above-described sample dispersion device, one in which the density change mechanism holds the holding member parallel along a vertical direction and also applied with voltage at a potential opposite to that of the sample particles can be cited.

Even in such a configuration, the density of sample particles to be held by the holding member held in the density change mechanism can be changed by changing the voltage of the density change mechanism, and therefore the dispersion state of the sample particles can be changed.

Note that in this case as well, multiple holding members may be prepared to form multiple measurement samples having mutually different sample particle dispersion states or one measurement sample in which multiple portions having different dispersion states are provided on one holding member may be formed.

As the above-described sample dispersion method, a sample dispersion method that introduces sample particles into a container, and disperses sample particles onto a holding member provided in the container to make the holding member hold the sample particles, and that includes: an injection step of injecting the sample particles into the container using a pressure difference; and a holding step of, using a density change mechanism adapted to make an electric field act on the sample particles introduced into the container, on a holding surface of the holding member by which the sample particles are to be held, forming multiple holding areas where the densities of sample particles are different, and making the holding member hold the sample particles can be cited.

Advantageous Effects of Invention

According to the present invention, a measurement sample in a dispersion state suitable for observation can be prepared without repreparing the measurement sample many times.

REFERENCE SIGNS LIST 1, 20, 30, 40 Sample dispersion device
9, 21, 42 Holding member
23, 31 Density change mechanism

DETAILED DESCRIPTION OF THE INVENTION

The sample dispersion device of the present invention is one for preparing a measurement sample that is to be observed with an electron microscope such as an SEM or a device such as an optical microscope, and also one that disperses sample particles so as to achieve a predetermined density gradient without classifying the sample particles. Note that a measurement sample in the present embodiment refers to one in which sample particles are dispersed having a predetermined density gradient on a holding member.

<First Embodiment>

A sample dispersion device 1 in a first embodiment will be described below.

Figure 1:
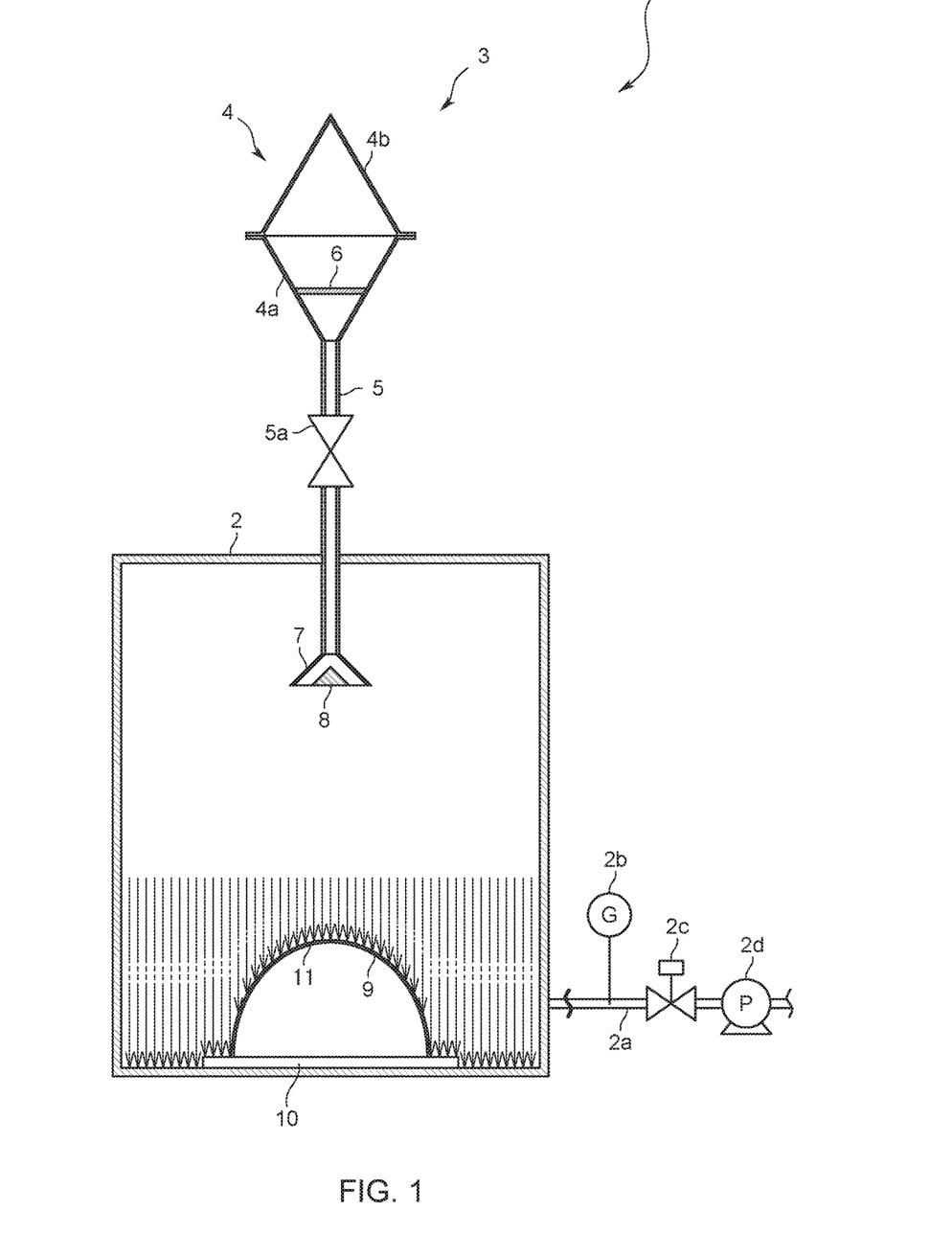
FIG. 1 is a schematic cross-sectional view of a sample dispersion device in a first embodiment of the present invention.

As illustrated in FIG. 1, the sample dispersion device 1 in the first embodiment includes: a container 2 into which sample particles are dispersed; and a sample introduction part 3 for introducing the sample particles into the container 2.

The container 2 is one capable of being brought into a vacuum state, and connected with an exhaust flow path 2a for exhausting air. The exhaust flow path 2a is provided with: a pressure gauge 2b for measuring the pressure inside the flow path; an exhaust valve 2c for opening/closing the exhaust flow path 2a; and a pump 2d for sucking air inside the container 2. Also, the sample introduction part 3 is connected to substantially the center of the upper part of the container 2.

The sample introduction part 3 includes: a sample supply mechanism 4 to which the sample particles are supplied; and a sample introduction pipe 5 connecting between the sample supply mechanism 4 and the container 2.

The sample supply mechanism 4 is configured to include a funnel-shaped sample container 4a and a cone-shaped lid 4b, and the sample container 4a is such that an outlet side having a decreased opening diameter is connected to the sample introduction pipe 5 and on an inlet side having an increased opening diameter, the lid 4b is detachably provided. When attaching the lid 4b to the sample container 4a, a space is formed inside the sample container 4a. In addition, in the sample container 4a, a filter 6 for filtering the sample particles is provided so as to block an opening.

The sample introduction pipe 5 is one such that the upper end part is opened to the outlet side of the sample container 4a having the decreased opening diameter, and the lower end art is opened inside the container 2. In addition, the sample introduction pipe 5 is provided with an open/close valve 5a for opening/closing the inside of the pipe. Further, the circumferential edge of the opening lower end of the sample introduction pipe 5 is provided with a cover 7 for preventing the sample particles from scattering toward the upper part of the container 2, and also a diffuser 8 is provided so as to face to the opening lower end of the sample introduction pipe 5. The diffuser 8 is one for diffusing the sample particles, and although not illustrated, held by the cover 7 using an appropriate holding member.

In addition, in the container 2, a holding member 9 adapted to hold dispersed sample particles is arranged fixed on a sample stage 10.

The holding member 9 has a holding surface 11 adapted to hold the sample particles, and is placed inside the container 2 with the holding surface 11 formed with multiple portions having mutually different tilt angles.

Specifically, the holding member 9 is a rectangular-shaped plate-like member, and formed of, for example, a flexible plastic plate. In addition, the holding member 9 is bent so as to shorten the distance between both mutually opposite ends present in a longer direction, and arranged forming a partially cylindrical shape inside the container 2. Further, a surface (upper surface) facing to the sample introduction part 3 side serves as the holding surface 11. The holding surface 11 is formed by being stuck with carbon tape.

In addition, since the holding surface 11 is bent so as to shorten the distance between both mutually opposite ends present in the longer direction, and arranged forming the arc shape inside the container 2, the multiple portions having the mutually different tilt angles are mutually adjacently arranged on the holding surface 11. Also, the multiple portions have a predetermined length (the same length as the length of the holding member 9 in the longer direction) in a direction perpendicular to a direction of the mutually adjacent arrangement.

The actions of the sample dispersion device 1 of the first embodiment configured as described above will be described.

When a sample is loaded into the sample container 4a in a state where the open/close valve 5a and the exhaust valve 2c are closed, the sample particles are filtered by the filter 6 and also stay before the open/close valve 5a of the sample introduction pipe 5. Then, when opening the exhaust valve 2c and activating the pump 2d, air inside the container 2 is sucked and the inside of the container 2 is gradually depressurized. After that, at the time of reaching a vacuum state, the exhaust valve 2c is closed and the pump 2d is stopped.

Subsequently, when opening the open/close valve 5a, the sample particles in the sample container 4a kept at atmospheric pressure are strongly sucked toward the container 2 side in the vacuum state and move down through the sample introduction pipe 5. At this time, air remaining in the sample container 4 is also sucked toward the container 2 side, whereby the pressure difference between the sample container 4a and the container 2 causes a high-speed air current near the opening lower end of the sample introduction pipe 5, and due to the air current, the sample particles are introduced into the container 2 while being vigorously injected. This step corresponds to an injection step in claims.

The injected sample particles collide with the diffuser 8, and aggregates are finely pulverized. Also, the cover 7 prevents diffusion to the upper part of the container 2, and the sample particles fall downward while uniformly diffusing without being classified. Then, the sample particles are held in a dispersion state by the holding surface 11 of the holding member 9. This step corresponds to a holding step in claims.

Figure 2:
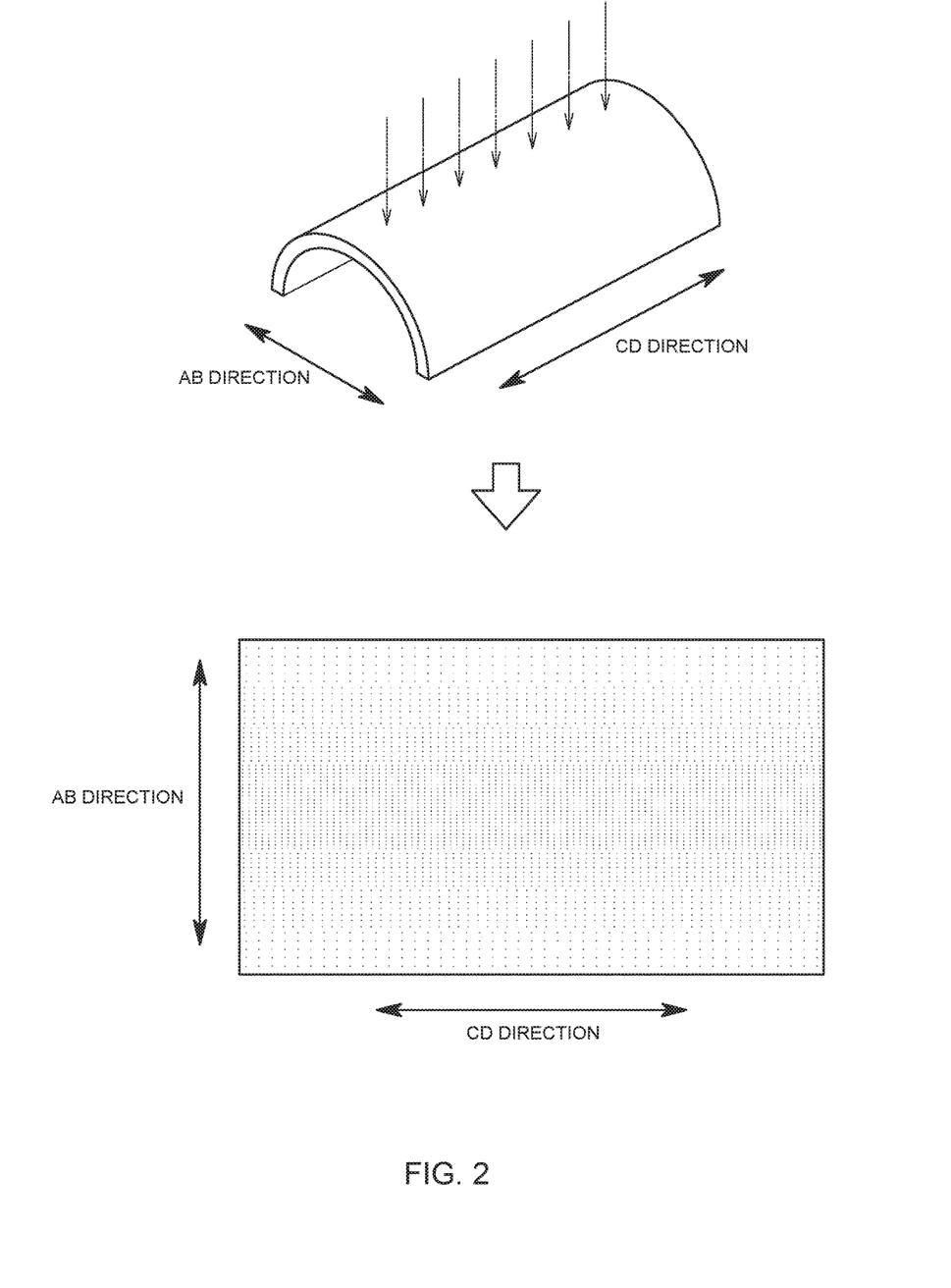
FIG. 2 is a schematic diagram illustrating a holding member in the first embodiment of the present invention.

When the sample particles are held by the holding member 9, the holding member 9 is taken out of the container 2 and restored to a horizontal flat plate state. As a result, as illustrated in FIG. 2, in the direction (in an AB direction) in which the multiple portions are mutually adjacently arranged, sample particles are densely held in substantially the central portion, and in both end portions, sample particles are sparsely held. In addition, the sample particles exhibit continuous changes from a dense portion to sparse portions. Also, in the direction perpendicular to the direction in which the multiple portions are mutually adjacently arranged (in a CD direction perpendicular to the AB direction), sample particles are held at a substantially uniform density.

Note that in FIG. 2, the dispersion state of the sample particles seems to be illustrated as if it changes stepwise; however, the dispersion state of the sample particles continuously changes.

In the sample dispersion device 1 in the first embodiment configured as described above, in order to provide a density gradient to the dispersion state of the sample particles, the sample particles are injected and also the multiple portions having the mutually different tilt angles are provided on the holding surface 11 of the holding member 9. This configuration makes it possible to provide the density gradient to the dispersion state of the sample particles because when the sample particles uniformly diffused by the injection are held by the holding member 9, the amount of sample particles is changed depending on a tilt angle of the holding surface 11. For this reason, by changing an observation area of the holding member 9 in an electron microscope, a dispersion state most suitable for observation can be obtained, and therefore a measurement sample can be prepared by dispersing once without repreparing the measurement sample many times. Also, since the sample particles are injected, the sample particles can be dispersed on the holding member 9 faster than spontaneous precipitation, and also can be prevented from being classified.

In addition, since the multiple portions having the mutually different tilt angles provided on the holding surface 11 of the holding member 9 are adjacently arranged, sets of sample particles in different dispersion states are continuously held, and an operator can observe the dispersion states stepwise and easily make the observation with a device such as an electron microscope or an optical microscope.

Also, since the multiple portions have the predetermined length in the direction perpendicular to the direction of the mutually adjacent arrangement, an observation area of sample particles dispersed in the same dispersion state can be expanded.

In addition, since the holding member 9 is one forming the partially cylindrical shape, the density of sample particles can be continuously changed and also the dispersion state can be more finely changed, thus making it possible to prepare a measurement sample in a dispersion state more suitable for observation by dispersing once.

Also, since the diffuser 8 can prevent the vigorously injected sample particles from directly colliding with the holding member 9, the surface of the holding member 9 can be prevented from being damaged by the sample particles.

Further, it is known that as the diameter of a sample particle decreases, a falling time becomes longer. Under atmospheric pressure, when the particle diameter of a sample particle is 1 µm, the time to fall 1 m is 60 s, whereas when the particle diameter of a sample particle is 100 nm, the time to fall 1 m is 6000 s. On the other hand, under vacuum, when the particle diameter of a sample particle is 1 µm, the time to fall 1 m is 0.6 s, whereas when the particle diameter of a sample particle is 100 nm, the time to fall 1m is 60 s, and as compared with under atmospheric pressure, under vacuum, the arrival time of a sample particle at the holding member 9 is significantly reduced. Note that since in the present embodiment, the sample particles are dispersed under vacuum, the time necessary to prepare the measurement sample can be reduced. Also, the sample particles held by the holding member 9 can be prevented from being disturbed by an air current.

In addition, since the filter 6 is provided in the sample container 4a, the sample introduction pipe 5 can be prevented from being clogged with aggregated sample particles.

<Second Embodiment>

A sample dispersion device 20 in a second embodiment will be described below.

Note that the same parts as those in the first embodiment are denoted by the same reference signs, and description thereof is omitted.

Figure 3:
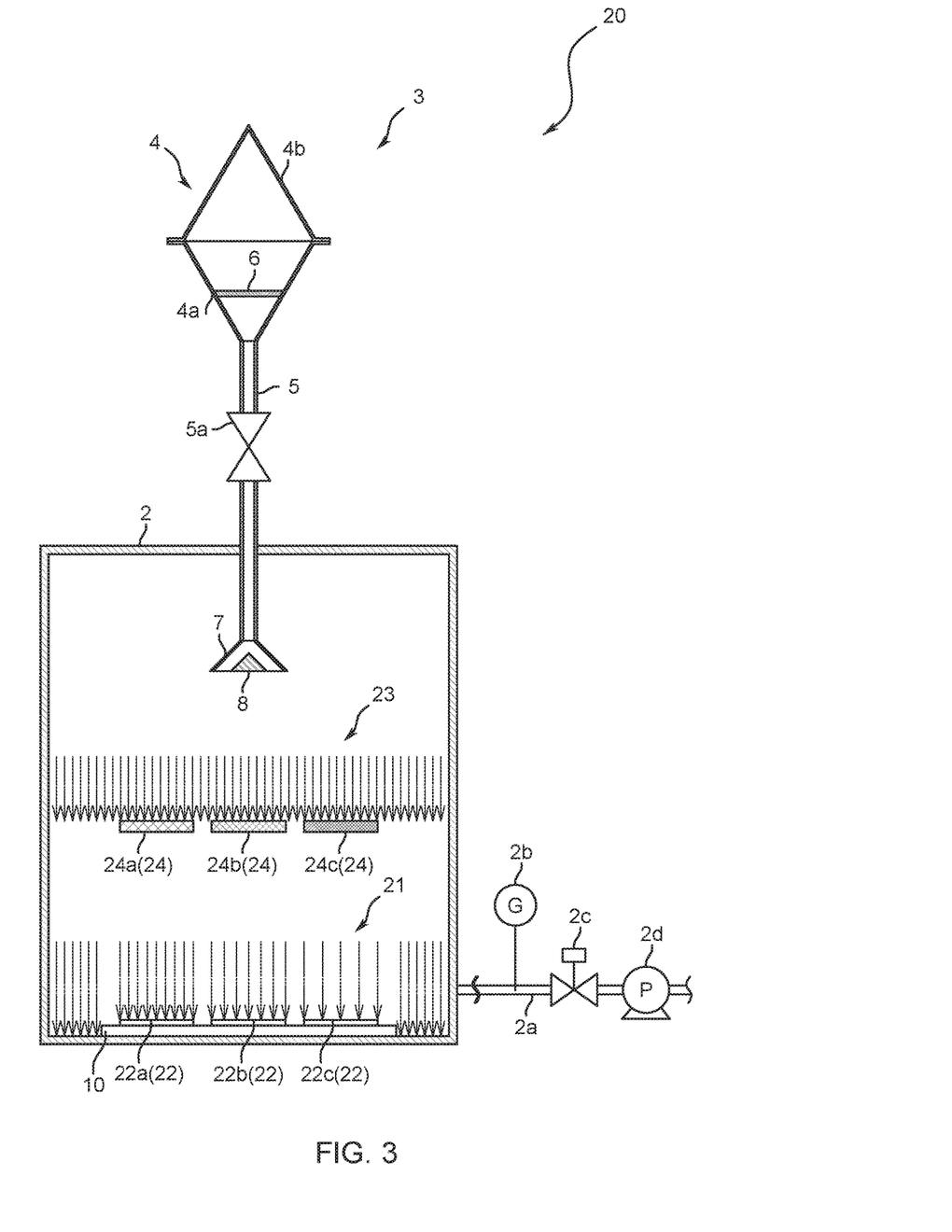
FIG. 3 is a schematic cross-sectional view of a sample dispersion device in a second embodiment of the present invention.

As illustrated in FIG. 3, the sample dispersion device 20 in the second embodiment includes, in addition to a container 2 into which sample particles are dispersed, a sample introduction part 3 for introducing the sample particles into the container 2, and holding members 21 adapted to hold dispersed sample particles, a density change mechanism 23 adapted to make an electric field act on the sample particles introduced into the container 2, and thereby on holding surfaces 22, form multiple holding areas where the densities of sample particles to be held are different.

The density change mechanism 23 is one that is arranged between the sample introduction part 3 and the holding members 21, and applied with voltage at a potential opposite to that of the sample particles. Specifically, the density change mechanism 23 is configured to include multiple collection plates 24 (24a, 24b, and 24c). The collection plates 24 are formed of a mesh-shaped metallic member of which one mesh is an opening sufficiently larger than the particle size of a sample particle, and connected with an unillustrated voltage supply mechanism. The voltage supply mechanism is one adapted to load voltage at a potential opposite to that of the sample particles on the collection plates 24, and load different voltages on the collecting plates 24, respectively. Also, in the present embodiment, the multiple holding surfaces 22 (22a, 22b, and 22c) of the holding members 21 are formed, and the collecting plates 24 are arranged so as to respectively face to the holding surfaces 22.

The actions of the sample dispersion device 20 of the second embodiment configured as described will be described below.

When the sample particles are dispersed, parts of the sample particles are collected by the collecting plates 24 having a potential opposite to that of the sample particles. At this time, the amount of sample particles collected by the collecting plate 24 increases in proportion to the intensity of voltage loaded on the collection plate 24. For this reason, as the voltages loaded on the collecting plates 24 are increased, the dispersion states of sample particles held by the holding members 21 become sparse.

In the sample dispersion device 20 of the second embodiment configured as described above, the density change mechanism 23 can change the dispersion state of sample particles, and therefore a measurement sample in a dispersion state most suitable for observation can be prepared by dispersing once without repreparing the measurement sample many times.

Figure 4:
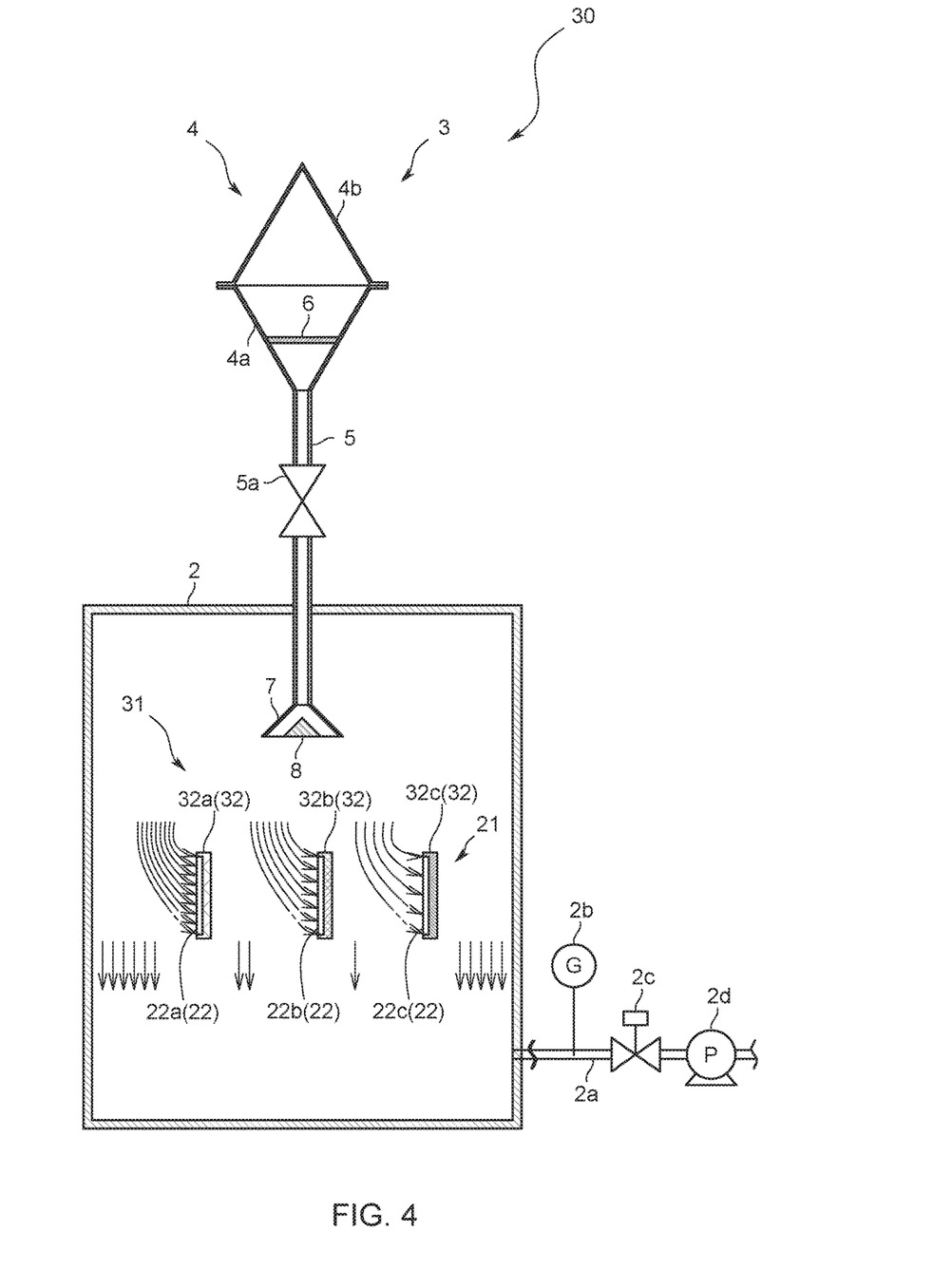
FIG. 4 is a schematic cross-sectional view of a sample dispersion device in a third embodiment of the present invention.

Also, since the density change mechanism 23 is one that is arranged between the sample introduction part 3 and the holding members 21 and applied with voltage at a potential opposite to that of the sample particles, the density change mechanism 23 arranged between the sample introduction part 3 and the holding members 21 can collect sample particles and change the amount of the collected sample particles by changing the voltage, thus making it possible to change the densities of sample particles to be held on the holding members 21 to change the dispersion states, respectively.

<Third Embodiment>

A sample dispersion device 30 in a third embodiment will be described below.

Note that the same parts as those in the first embodiment and the second embodiment are denoted by the same reference signs, and description thereof is omitted.

As illustrated in FIG. 4, in the sample dispersion device 30 in the third embodiment, a density change mechanism 31 is different from that in the second embodiment.

The density change mechanism 31 in the third embodiment is one that holds holding members 21 parallel along a vertical direction and also applied with voltage at a potential opposite to that of sample particles. Specifically, the density change mechanism 31 is configured to include multiple fixing holders 32 (32*a*, 32*b*, and 32*c*) respectively adapted to fix surfaces opposite to holding surfaces 22 (22*a*, 22*b*, and 22*c*) of the holding members 21 so as to make the holding surfaces 22 parallel to a falling direction (vertical direction) of the sample particles falling. Also, the fixing holders 32 are connected with an unillustrated voltage supply mechanism, and the voltage supply mechanism is one that loads voltage at the potential opposite to that of the sample particles on the fixing holders 32 and loads different voltages on the fixing holders 32, respectively. Note that as a configuration adapted to fix the holding members 21 to the fixing holders 32, for example, it may be configured to do the fixation through detachable adhesive sheets, or fit the holding members 21 into depressions provided in the fixing holders 32.

The actions of the sample dispersion device 30 of the third embodiment configured as described will be described below.

When the sample particles are dispersed, parts of the sample particles are sucked by the fixing holders 32 loaded with the opposite potential, and held by the holding surfaces 22 fixed to the fixing holders 32. At this time, since a voltage is loaded differently on each of the fixing holders 32, the amount of samples held by a holding surface 22 varies depending on each of the fixing holders 32, and as the voltage is increased, the dispersion state of sample particles held by a holding surface 22 becomes denser.

In the sample dispersion device 30 in the third embodiment configured as described above, since the density change mechanism 31 is one that holds the holding members 21 parallel along the vertical direction and is also applied with voltage at a potential opposite to that of the sample particles, by changing the voltage of the density change mechanism 31, the densities of sample particles held by the holding members 21 held in the density change mechanism 31 can be changed to change the dispersion states of sample particles.

<Fourth Embodiment>

A sample dispersion device 40 in a fourth embodiment will be described below.

Note that the same parts as those in the first embodiment, second embodiment, and third embodiment are denoted by the same reference signs, and description thereof is omitted.

Figure 5:
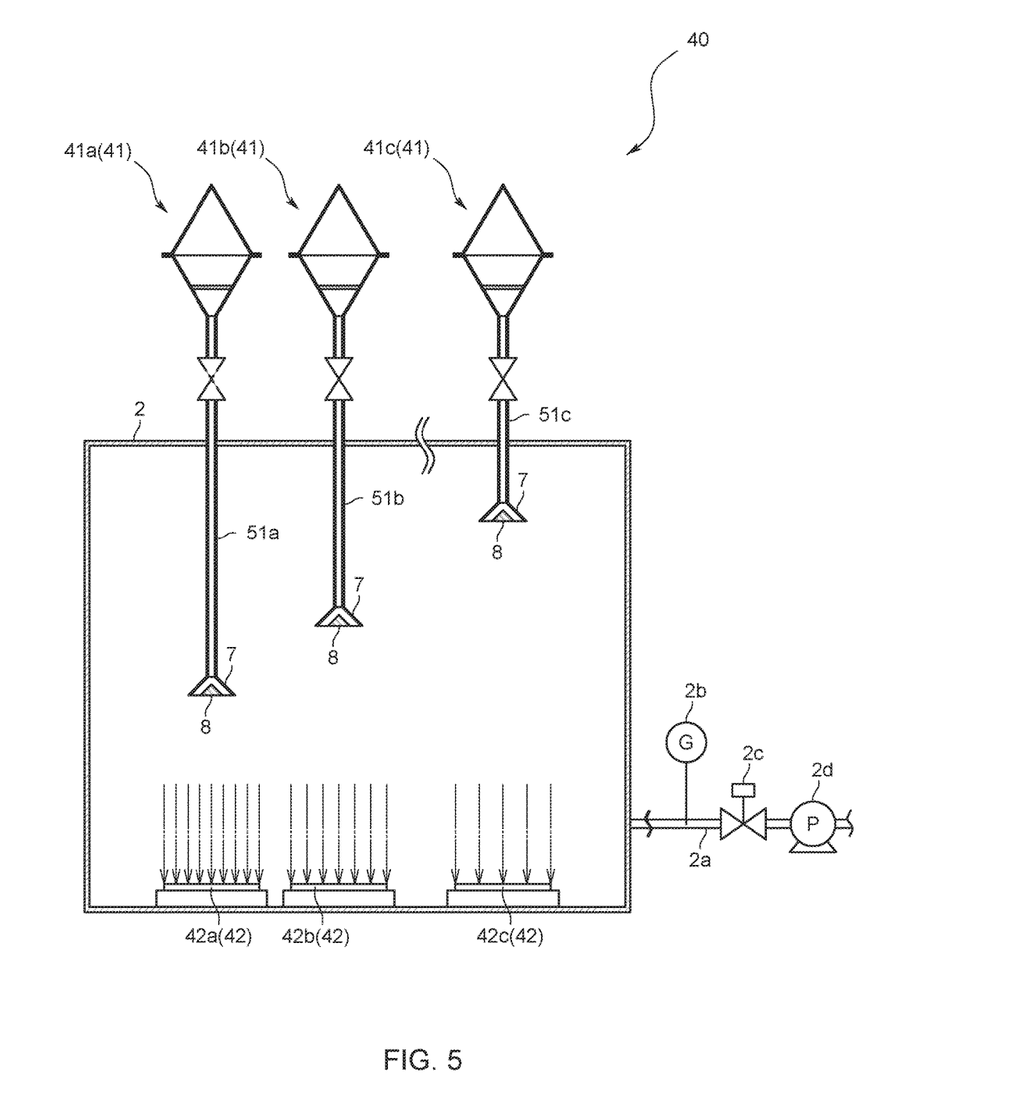
FIG. 5 is a schematic cross-sectional view of a sample dispersion device in a fourth embodiment of the present invention.

As illustrated in FIG. 5, the sample dispersion device 40 in the fourth embodiment includes: a container 2 into which sample particles are dispersed; multiple sample introduction parts 41 (41a, 41b, and 41c) for introducing the sample particles into the container 2; and multiple holding members 42 (42a, 42b, and 42c) adapted to hold dispersed sample particles. The multiple holding members 42 (42a, 42b, and 42c) are arranged so as to respectively face to the above-described multiple sample introduction parts 41 (41a, 41b, and 41c).

In addition, the sample introduction parts 41 are respectively connected with sample introduction pipes 51 (51a, 51b, and 51c) having different pipe lengths. Also, opening ends from which the sample introduction pipes 51 inject the sample particles are respectively provided with covers 7 and diffusers 8.

In the sample dispersion device 40 in the fourth embodiment configured as described, since the pipe lengths of the sample introduction pipes 51 (51a, 51b, and 51c) are different, as the distance between a holding member 42 and the opening end of a corresponding sample introduction pipe 51 is decreased, the dispersion state of sample particles held by the holding member 42 can be made denser, whereas as the distance between a holding member 42 and the opening end of a corresponding sample introduction pipe 51 is increased, the dispersion state of sample particles held by the holding member 42 can be made sparser. For this reason, by changing the pipe length of a sample introduction pipe 51, the dispersion state of sample particles held by a corresponding holding member 42 can be changed, and therefore a measurement sample in a dispersion state most suitable for observation purpose can be prepared without repreparing the measurement sample many times.

Note that the present invention is not limited to any of the above-described embodiments.

For example, the sample dispersion device may be configured to, in the sample dispersion device of the first embodiment, form the holding member in a flat plate shape, and also change the amount of samples dispersed from the opening per unit time.

Also, the sample dispersion device may be one that changes the dispersion state of sample particles by changing the dispersion amount of sample particles from the sample introduction part per unit time.

Figure 6:
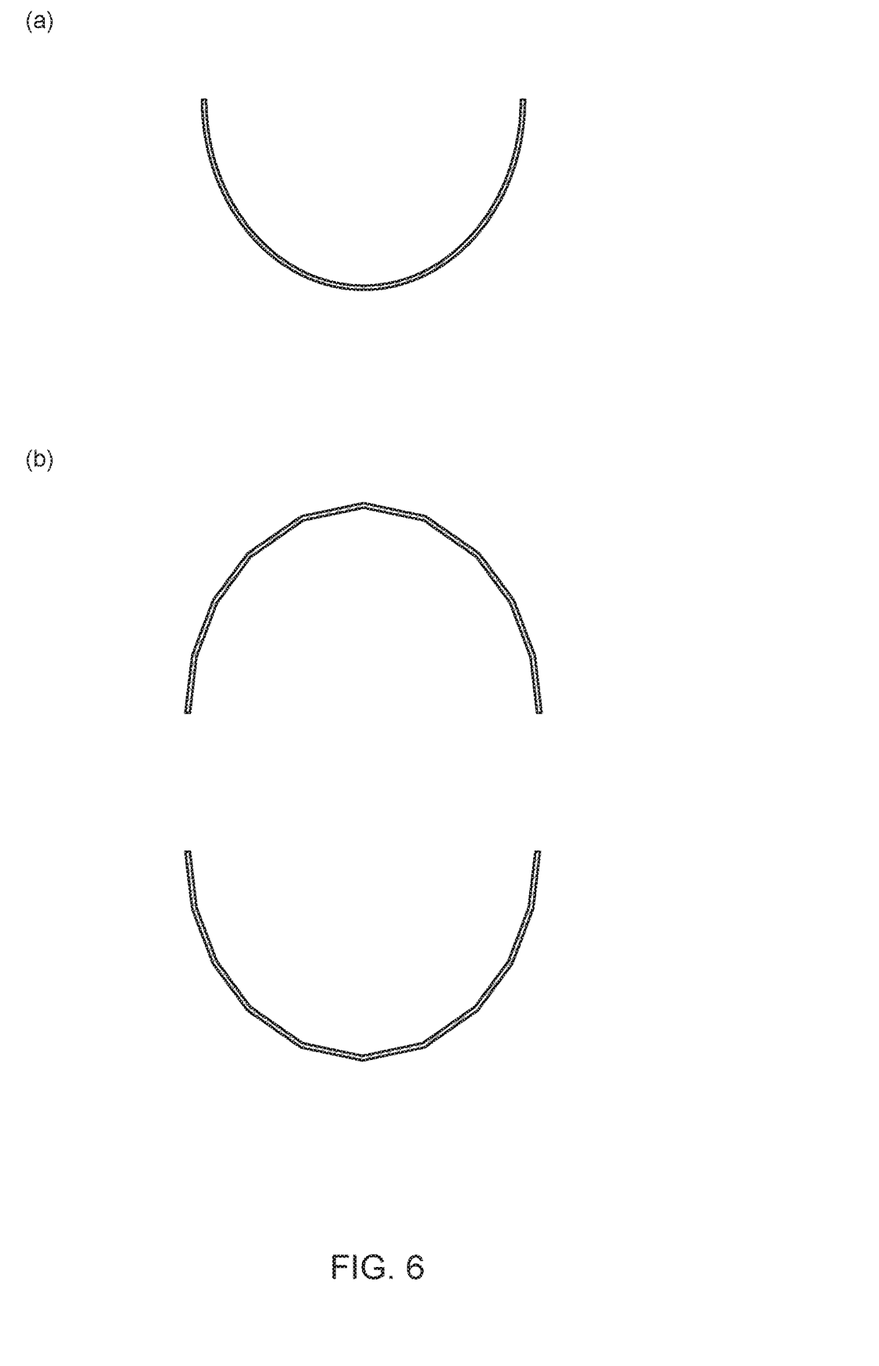
FIG. 6 is a schematic diagram illustrating holding members in other embodiments of the present invention.

Further, in the sample dispersion device of the first embodiment, the shape of the holding member may be a concave shape formed by, as illustrated in FIG. 6(a), bending the holding member in valley fold. Also, as illustrated in FIG. 6(b), the holding member may be configured not to have an arc shape in a cross-sectional view but to have a polygonal shape in a cross-sectional view. Note that in the first embodiment, the holding surface having the multiple portions having the mutually different tilt angles includes one having an arc shape, elliptical shape, or spline shape of which a tilt angle smoothly changes.

In addition, in the above-described first embodiment, the holding member is one forming the flat plate shape, but may be one forming a semicircular shape in a cross-sectional view by being bent so as to shorten the distance between the both mutually opposite ends present in the longer direction. For the holding member, a plastic member can also be used or a non-plastic member can also be used. Further, the holding member forming the semicircular shape is one that is taken out of the container after the sample particles have been dispersed onto the holding surface, and then directly inserted into a device such as an electron microscope or an optical microscope for observation.

Also, in the fourth embodiment, the opening ends of the sample introduction pipes from which the sample particles are injected are respectively provided with the covers and the diffusers; however, the fourth embodiment may be configured without providing any cover or diffuser.

Further, any of the above-described first to fourth embodiments is one adapted to disperse the sample particles by bringing the inside of the container to vacuum as well as bringing the sample introduction part or the sample introduction parts to atmospheric pressure to provide the pressure difference between the inside of the container and the sample introduction pipe or the sample introduction pipes, but may be one adapted to inject the sample particles by bringing the inside of the container to ordinary pressure as well as pressurizing the sample introduction part or the sample introduction parts to provide the pressure difference between the inside of the container and the sample introduction pipe or the sample introduction pipes.

In addition, in any of the second to fourth embodiments, the sample particles may be dispersed onto the holding members by spontaneous precipitation. However, injecting the sample particles using the pressure difference makes it possible to more suitably disperse the sample particles.

Also, in any of the above-described first to fourth embodiments, the holding surface or the holding surfaces are formed by being stuck with carbon tape; however, the sample particles may be held by the holding surface or the holding surfaces by static electricity generated between the holding member or the holding members and the sample particles.

The present invention can be variously modified without departing from the scope thereof.

INDUSTRIAL APPLICABILITY

The present invention can provide a sample dispersion device capable of preparing a measurement sample in the most suitable dispersion state without repreparing the measurement sample many times.

The invention claimed is:

1. A sample dispersion device comprising:
a container into which sample particles are introduced using a pressure difference; and
a holding member provided in the container, the holding member holding the sample particles that have been introduced into the container using the pressure difference, wherein:
the holding member has a holding surface made to hold the sample particles; and
the holding surface has multiple portions having mutually different tilt angles.

2. The sample dispersion device according to claim 1, wherein
the multiple portions formed on the holding surface are mutually adjacently arranged, and have a predetermined length in a direction perpendicular to a direction of the mutually adjacent arrangement.

3. The sample dispersion device according to claim 1, wherein
the holding member forms a partially cylindrical shape.

4. A sample dispersion method that introduces sample particles into a container, and disperses sample particles onto a holding member provided in the container to make the holding member hold the sample particles, the sample dispersion method comprising:
an injection step of injecting the sample particles into the container using a pressure difference; and
a holding step of making the holding member hold the injected sample particles, wherein
in the holding step, the holding member provided with a holding surface having multiple portions having mutually different tilt angles is made to hold the sample particles.

5. The sample dispersion device according to claim 1, wherein the holding surface is configured to adhere to the sample particles.

6. The sample dispersion device according to claim 5, wherein the holding surface includes a carbon tape for adhering to the sample particles.

7. The sample dispersion device according to claim 5, wherein the holding surface is applied with a voltage potential opposite to that of the sample particles.

8. The sample dispersion device according to claim 1, wherein the sample particles on the holding surface are observable in an electron microscope or an optical microscope.

* * * * *